United States Patent
Thomson

(10) Patent No.: US 7,049,339 B2
(45) Date of Patent: May 23, 2006

(54) COMPOSITION FOR THE TREATMENT OF DISEASES WHICH AFFECT ANIMALS' HOOVES

(75) Inventor: William Thomson, Turriff (GB)

(73) Assignee: Forty Eight Shelf (80) Limited, Glasgow (GB)

( * ) Notice: Subject to any disclaimer, the term of this patent is extended or adjusted under 35 U.S.C. 154(b) by 50 days.

(21) Appl. No.: 10/480,574

(22) PCT Filed: Jun. 14, 2002

(86) PCT No.: PCT/GB02/02486

§ 371 (c)(1),
(2), (4) Date: Dec. 12, 2003

(87) PCT Pub. No.: WO02/102352

PCT Pub. Date: Dec. 27, 2002

(65) Prior Publication Data

US 2004/0175433 A1    Sep. 9, 2004

(30) Foreign Application Priority Data

Jun. 15, 2001 (GB) .................................... 0114677
May 15, 2002 (GB) .................................... 0211067

(51) Int. Cl.
*A61K 33/34*    (2006.01)
*A61K 33/30*    (2006.01)
*A61K 33/14*    (2006.01)
*A61K 31/19*    (2006.01)

(52) U.S. Cl. ..................... 514/494; 514/23; 514/54; 514/60; 514/499; 514/557; 424/630; 424/642; 424/685

(58) Field of Classification Search ................ 424/630, 424/685, 642; 514/23, 54, 60, 557, 494, 514/499
See application file for complete search history.

(56) References Cited

U.S. PATENT DOCUMENTS

| | | | | |
|---|---|---|---|---|
| 4,046,886 A | * | 9/1977 | Smith | 514/152 |
| 4,278,789 A | * | 7/1981 | Birkenmeyer | 536/16.3 |
| 4,822,595 A | * | 4/1989 | Corliss et al. | 424/61 |
| 5,234,955 A | * | 8/1993 | Ray et al. | 514/592 |
| 5,651,977 A | | 7/1997 | Kross | |
| 5,780,064 A | * | 7/1998 | Meisters et al. | 424/616 |

FOREIGN PATENT DOCUMENTS

| | | |
|---|---|---|
| DE | 34 43 985 A1 | 6/1986 |
| EP | 0 966 974 A1 | 12/1999 |
| WO | WO 95/28164 A1 | 10/1995 |
| WO | WO 01/37828 A1 | 5/2001 |

OTHER PUBLICATIONS

The Merck Index, 12 Edition, 1996, pp. 822-823.*

* cited by examiner

*Primary Examiner*—James O. Wilson
*Assistant Examiner*—Ganapathy Krishnan
(74) *Attorney, Agent, or Firm*—Drinker Biddle & Reath LLP; Daniel A. Monaco

(57) ABSTRACT

A composition for treating a disease affecting the hoof of an animal comprising an active ingredient and a colloid former is described. The active ingredient may comprise zinc sulphate, copper sulphate, an organic acid, an alkali metal salt or a mixture thereof. The composition as disclosed has the advantage that it is more effective at applying an active ingredient to a hoof than a conventional, non-colloid system.

11 Claims, 1 Drawing Sheet

COMPOSITION FOR THE TREATMENT OF DISEASES WHICH AFFECT ANIMALS' HOOVES

Figure 1:
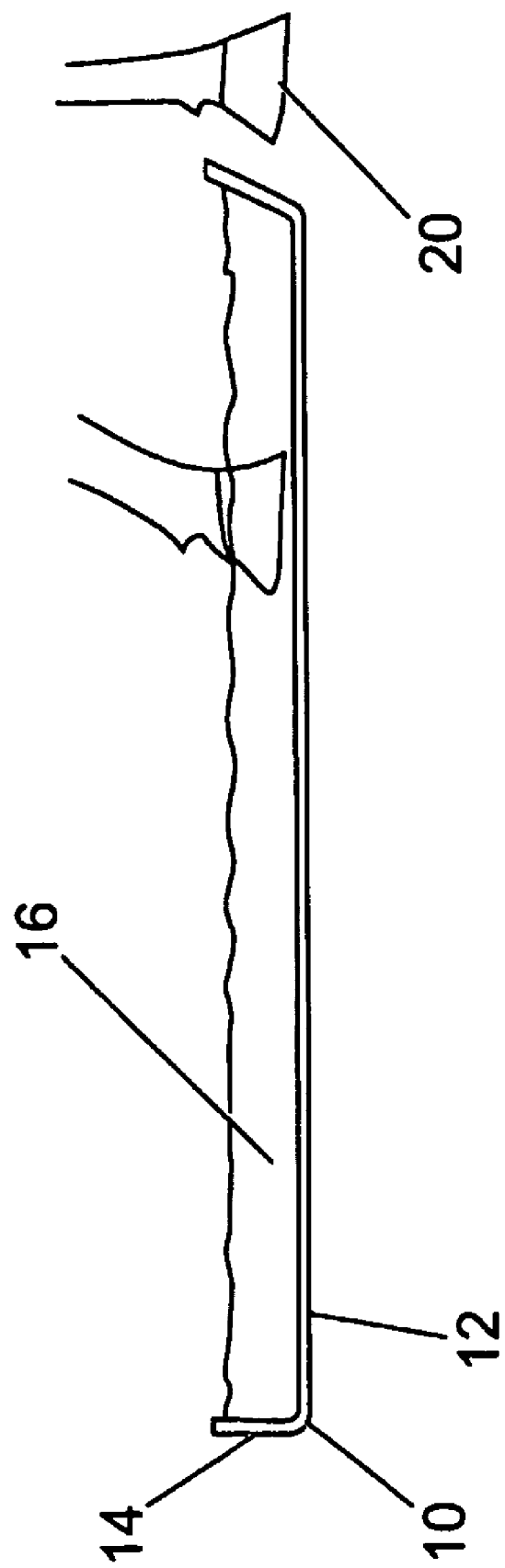

The present invention relates to a composition, particularly but not exclusively to a composition for the treatment of diseases which affect animals' hooves.

Many ungulates suffer from diseases affecting their hooves. This is of particular concern to the cattle industry because lameness is the third most common reason for the culling of dairy cattle. Moreover, cows cured of lameness often suffer recurring infections especially during lactation. Typically 15 to 18% of a herd is affected at one time by lameness.

It is common for lameness to be treated by administration of antibiotics. Widespread use of antibiotics may, however, lead to the emergence of antibiotic resistant pathogens and consequently antibiotic resistant infections, which are clearly a matter of public concern. Furthermore, antibiotics are generally prohibitively expensive.

One of the most common causes of lameness is digital dermatitis. This is commonly treated through the use of a liquid footbath containing a water based solution of copper sulphate. To be effective the animal's hooves must be kept in the copper sulphate solution footbath for a protracted period of time, which typically varies from several minutes to half an hour. It is very difficult and inconvenient to keep animals in a footbath for such a length of time. Moreover, the number of animals which can be treated at one time is limited, such treatment is therefore time consuming and consequently costly. Other diseases affecting animal's hooves are also treated by the use of liquid footbaths containing various active ingredients. For example, zinc sulphate is often used in a footbath to treat foot rot. Such treatments have, however, proven to be of limited efficacy, particularly in the treatment of digital dermatitis. Such footbaths may also represents a health risk to the animals if they happen to drink their contents.

We have found that using a viscous rather than a liquid footbath performs much better in preventing and combating hoof diseases.

STATEMENT OF THE INVENTION

According to one aspect of the present invention there is provided a composition comprising at least one active ingredient, such as an antiseptic or disinfectant, and a colloid former. Preferably the active ingredient is a zinc salt, suitably zinc sulphate.

The composition may further comprise a copper salt (such as copper sulphate), an organic acid, an alkali metal salt (e.g. potassium or sodium chloride) or a combination thereof as active ingredients.

Preferably the composition is a topical composition which is viscous and adheres at least partially to a surface which it contacts. Preferably the composition adheres to an animal's hoof. In this respect it is found that it is advantageous if the composition is a colloid.

The term "colloidal" as used herein refers to viscous compositions such as gels, sols and emulsions and other such compositions which generally have a viscosity higher than that of water.

Thus, another object of the invention is a colloidal composition which comprises the composition described above and a liquid, preferably water. Advantageously the colloidal mixture comprises about 85 to 95% of water and has a homogeneous mud-like texture. The presence of the colloid former may act to increase both the viscosity of the composition and its adhesive properties when the liquid is present. The viscosity of the mixture is chosen so that once a layer has adhered onto the hooves it dries quickly. Clearly the drying time depends on the volatility of the liquid (which is typically water), but generally to enable rapid drying the layer of colloidal composition will need to be relatively thin.

A colloid former is an amorphous solid which disperses in a suitable solvent to form a lyophilic sol. As mentioned above, gels can be described as a form of colloidal system and, as such, the expression "colloid formers" encompasses gelling agents.

A suitable colloid former may be clay-based, for instance sepiolite or kaolin. Alternatively the colloid former may be starch, cellulose, lanolin, an oil or a combination thereof. Preferably the colloid former used is sepiolite.

Alternatively the colloid former can be a gelling agent, particularly xanthan gum or alginate, or a combination thereof. Where xanthan gum is used it is found that mixing of the composition is easier than when clay-based compositions are used. In addition, xantham gum has the advantage that it is generally considered to be non-toxic and is in fact used in food manufacture.

The organic acid suitably comprises 2 to 10 carbon atoms. Preferably the organic acid is citric acid. Other suitable organic acids include lactic acid, maleic acid and fumaric acid.

Typically a dry composition made according to the invention comprises at least 10 to 90% by weight of zinc salt (for example zinc sulphate), suitably 15 to 60% by weight, preferably 20 to 30% by weight.

Typically a dry composition made according to the invention comprises at least 15 to 90% by weight of copper salt (for example copper sulphate), preferably 20 to 60% by weight, more preferably 30 to 50% by weight.

Typically a dry composition made according to the invention comprises at least 10 to 90% by weight of a alkali metal salt (typically sodium or potassium chloride), preferably 15 to 60% by weight, more preferably 20 to 30% by weight.

Typically a dry composition made according to the invention comprises at least 0.1 to 15% by weight of an organic acid (suitably citric acid), preferably 1 to 10% by weight, more preferably 2 to 4% by weight.

Typically a dry composition made according to the invention comprises at least 5 to 50% by weight of a colloid former, preferably 5 to 40% by weight, more preferably 5 to 20% by weight.

Preferably the composition contains approximately (by weight):
15% SPLF (sepiolite)
27.5% sodium chloride
27.5% copper sulphate
2.5% citric acid
27.5% zinc sulphate An alternative composition contains approximately (by weight):
7% xanthan gum
30% sodium chloride
30% copper sulphate
3% citric acid
30% zinc sulphate Suitably the composition may further comprise additives like herbal oils, formaldehyde, lincomycin, spectinomycin, oxytetracycline, formalin, sulfonamide, citrus extracts, calcium stearate or a combination thereof.

The composition of the invention may comprise a dedusting agent such as an oil. Both mineral and vegetable oils can be considered. Mineral oils and especially mineral white oils such as liquid paraffin oil are preferred. Other organic oils such as vegetable oils, particularly soya or sunflower oil, may be suitable alternatives.

Typically the dedusting agent comprises 0.5 to 25% by weight of the composition, preferably 1 to 20% by weight of the composition, more preferably 1 to 10% by weight of the composition.

The composition of the invention can be used as an antiseptic or disinfectant.

Advantageously the composition of the invention is used for the treatment or the prevention of hoof infections particularly scald, foul in the foot (including "super foul"), interdigital dermatitis, interdigital growth, digital dermatitis, sole and heel erosion, sole ulcers, bovine foot root, interdigital growth, foot warts, purulent arthritis or serous arthritis.

A composition according to the present invention is particularly suitable for treating digital dermatitis, scold or foot rot.

Advantageously the composition is coloured (that is, the composition includes a dye or colouring agent) and is clearly visible on a hoof when dried.

According to a further aspect of the present invention there is provided a method of treating a disease affecting the hoof of an animal by providing a composition comprising an active ingredient and a colloid former and coating said composition onto the animal's hoof. The composition adheres to the animal's hoof and is of viscosity such that the layer adhered to the hoof is of a desired thickness. Preferably the thickness of the layer is such that a therapeutically beneficial amount of the active ingredient is bound to the hoof, but not so thick that drying takes an inconvenient length of time. Advantageously the active ingredient of the composition is one as described above. The disease treated may be scald, foul in the foot (including "Super Foul"), interdigital dermatitis, interdigital growth, digital dermatitis, sole and heel erosion, sole ulcers, bovine foot root, interdigital growth, foot warts, purulent arthritis or serous arthritis, solar ulcer, white line disease, acute laminitis, punctured sole, heel horn erosion, overgrown claws. This method is particularly useful for treating digital dermatitis, scold or foot rot.

Suitable colloid formers include sepiolite, kaolin, starch, cellulose, lanolin, oil, xanthan gum, alginate or a combination thereof.

Advantageously the composition may be applied by walking an animal through a footbath containing the composition. Alternatively the composition may be sprayed or painted directly onto the animal's hoof.

A further object of the present invention is a veterinary composition comprising zinc sulphate, an organic acid, a salt (particularly sodium or potassium chloride) and copper sulphate.

Typically at least 10 to 90% by weight of the veterinary composition is zinc sulphate, suitably 15 to 60% by weight, preferably 20 to 40% by weight. Typically at least 15 to 90% by weight of the veterinary composition is copper sulphate, preferably 20 to 60% by weight, more preferably 30 to 50% by weight. Typically at least 10 to 90% by weight of the veterinary composition is potassium or sodium chloride, preferably 15 to 60% by weight, more preferably 20 to 30% by weight. Typically at least 0.1 to 15% by weight of the veterinary composition is citric acid, preferably 1 to 10% by weight, more preferably 2 to 4% by weight.

A further object of the invention is the use of the above veterinary composition in a method to treat an animal's hoof which method comprises the step of applying the veterinary composition onto an animal's hoof. The composition may be used either prophylactively or curatively.

Embodiments of the present invention will now be described, by way of example only, with reference to the examples and accompanying drawing, in which:

FIG. 1 shows a schematic side elevation of a animal footbath containing a composition according to the invention.

EXAMPLE 1

A dry mixture of approximately:

3.75 kg SPLF (sepiolite);
6.875 kg sodium chloride;
6.875 kg copper sulphate;
0.625 kg citric acid; and
6.875 kg zinc sulphate was prepared by mixing together the above ingredients using a power mixer. About 175–200 litres of pressurised water was injected to the mixture under pressure. A smooth sepiolite-based colloid composition of even consistency and of mud-like texture was formed.

Referring to FIG. 1, the colloid obtained according to Example 1 was poured into a cattle footbath 10 having a rectangular base portion 12, and four side portions 14 extending approximately vertically therefrom.

In operation, cattle are guided into the footbath 10 shown in FIG. 1 and walked along the length of the footbath 10, through the sepiolite-based colloid composition 16 formed as described above. The sepiolite-based colloid composition 16 is of sufficient viscosity such that a layer of the composition having a desired thickness sticks to the hooves 20 of the cattle. The sepiolite-based colloid composition 16 dries on the cattle hooves 20 within a few minutes. The animals are preferably kept in a concrete floored holding until drying is complete.

Instead of sepiolite, 1.2 kg of xanthan gum may be used. Such a composition is easier to mix as it can be prepared without the need for substantial mechanical mixing, for example the addition of water under pressure may be sufficient to obtain a suitably homogeneous colloid.

It is believed that the fact that the colloid composition sticks onto the hooves instead of being brushed off is particularly beneficial.

Modifications may be made to the operation of the footbath without departing from the scope of the invention. For example, any hoofed animal, in particular pigs, sheep or goats, may be guided into the footbath 10 and walked through the colloid composition 16.

EXAMPLE 2

An alternative variant of the composition includes a proportion of oil. Such a composition was prepared comprising 4 kg of SPLF, 6.65 kg of sodium chloride, 6.65 kg of copper sulphate, 0.625 kg citric acid, 6.875 kg zinc sulphate and 0.250 kg of liquid paraffin oil. These ingredients were again mixed together using a power mixer. To obtain the colloid, about 175–200 litres of pressurised water was injected into the mixture. A smooth colloid of even consistency was formed.

EXAMPLE 3

Comparison of Composition with and without Colloid Former

The following protocol was performed to demonstrate the efficacy of the colloid former in increasing the amount of active ingredient adhered to hooves.

Two footbaths were prepared containing compositions of the following specifications:

Footbath 1 (with Colloid Former):
- 3.75 kg SPLF (sepiolite);
- 6.875 kg sodium chloride;
- 6.875 kg copper sulphate;
- 0.625 kg citric acid; and
- 6.875 kg zinc sulphate,
  - in 175 litres of water.

Footbath 2 (without Colloid Former):
- 6.875 kg sodium chloride;
- 6.875 kg copper sulphate;
- 0.625 kg citric acid; and
- 6.875 kg zinc sulphate,
  - in 175 litres of water.

Samples of hooves from cattle were taken and analysed to determine their zinc content.

The cattle were then split into two groups and one group passed through each footbath. Following this they were then held in a concrete floored holding pen for approximately 10 minutes to allow drying.

Following drying, samples of hooves were again taken and analysed to determine their zinc content.

The average Zn content of the hoof samples from the two groups, pre- and post-treatment are shown in the table below:

| Mean Zn Content of Hoof Material (mg/kg) | | |
|---|---|---|
| | Post treatment | |
| Pre-treatment | Non-colloidal | Colloidal |
| 111 | 795 | 5865 |

These results clearly show that the colloidal composition is far more effective at administering an active ingredient to hooves than a non-colloidal equivalent; in this case the average dose was increased over seven fold.

As such, when the colloid former is used, it allows administration of greater amounts of active ingredient than a conventional, non-colloidal footbath containing the same concentration of active ingredient; thus there would be an expected increase in therapeutic activity.

Alternatively, use of the colloid former allows footbaths with far lower concentrations of active ingredient to achieve the same results as conventional footbaths; this not only significantly lowers costs, but also lessens the use and release of chemicals which may be harmful to the environment.

Modifications and improvements can be incorporated without departing from the scope of the invention.

What is claimed is:

1. A water-based viscous footbath for treating a disease affecting the hoof of an animal comprising at least one active ingredient and a colloid former, wherein said active ingredient comprises an antibiotic, disinfectant or a combination thereof, and said colloid former is clay-based.

2. A footbath according to claim 1 in which the colloid former is sepiolite.

3. A footbath according to claim 1 in which the active ingredient is selected from the group consisting of a zinc salt, a copper salt, an organic acid, an alkali metal salt and combinations thereof.

4. A footbath according to claim 3 in which the active ingredient is selected from the group consisting of zinc sulphate and copper sulphate.

5. A footbath according to claim 1 which comprises, by weight, 10–90% zinc sulphate, 15–90% copper sulphate, 10–90% alkali metal salt, 0.1–15% citric acid and 5–50% colloid former.

6. A footbath according to claim 5 which comprises, by weight, 15–60% zinc sulphate, 20–60% copper sulphate, 15–60% alkali metal salt, 1–10% citric acid and 5–40% colloid former.

7. A footbath according to claim 6 which comprises, by weight, 20–30% zinc sulphate, 30–50% copper sulphate, 20–30% alkali metal salt, 2–4% citric acid and 10–20% colloid former.

8. A composition according to claim 1 further comprising an additive selected from the group consisting of herbal oil, formaldehyde, lincomycin, spectinomycin, oxytetracycline, formalin, sulfonamide, citrus extracts, calcium stearate and combinations thereof.

9. A footbath according to claim 1 further comprising a dedusting agent.

10. A footbath according to claim 1 which is coloured and is clearly visible on a hoof when dried.

11. A method of treating a disease affecting the hoof of an animal, said method comprising contacting the hoof of the animal with a footbath according to claim 1, wherein the disease is selected from the group consisting of scald, foul in the foot, interdigital dermatitis, interdigital growth, digital dermatitis, sole and heel erosion, sole ulcers, bovine foot root, interdigital growth, foot warts, purulent arthritis and serous arthritis.

* * * * *